(12) United States Patent
Knopf

(10) Patent No.: US 10,653,474 B2
(45) Date of Patent: May 19, 2020

(54) SURGICAL VAPORIZATION ELECTRODE

(71) Applicant: OLYMPUS WINTER & IBE GMBH, Hamburg (DE)

(72) Inventor: Christoph Knopf, Luebeck (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 541 days.

(21) Appl. No.: 15/362,276

(22) Filed: Nov. 28, 2016

(65) Prior Publication Data

US 2017/0151010 A1 Jun. 1, 2017

(30) Foreign Application Priority Data

Nov. 26, 2015 (DE) .................. 10 2015 015 314

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/00107* (2013.01);
(Continued)

(58) Field of Classification Search
CPC .......... A61B 18/14; A61B 2018/00077; A61B 2018/00107; A61B 2018/00178;
(Continued)

(56) References Cited

U.S. PATENT DOCUMENTS 4,043,342 A * 8/1977 Morrison, Jr. ..... A61B 18/1402
606/48
5,827,274 A 10/1998 Bonnet et al.
(Continued)

FOREIGN PATENT DOCUMENTS

DE 29521028 U1 8/1996
DE 102007054438 A1 5/2009
(Continued)

OTHER PUBLICATIONS

Apr. 7, 2017 Search Report issued in European Patent Application No. 16198105.
(Continued)

*Primary Examiner* — Lee S Cohen
*Assistant Examiner* — Tigist S Demie
(74) *Attorney, Agent, or Firm* — Oliff PLC

(57) ABSTRACT

A working surface of the electrode head, designed to be essentially hemispherical in shape, is made of a suitable high-temperature-resistant metal. The electrode head is supplied with power via an electrical connecting line. The rear surface of the electrode head forming the sectional surface of the hemisphere is planar and is covered with an insulating cover made of a ceramic material. The transitional region from the working surface to the rear surface does not have an edge but instead is rounded with a minimum radius of curvature, which is substantially greater than one-thirtieth of the width, which corresponds to the hemisphere diameter (=twice the radius of the hemisphere), which is the dimension of the electrode head in the direction of its maximum extent. The relatively large radius of curvature prevents the main activity of the electrode from occurring at its boundary due to excessively high local current densities.

6 Claims, 1 Drawing Sheet

(52) U.S. Cl.
CPC ............ *A61B 2018/00178* (2013.01); *A61B 2018/00601* (2013.01); *A61B 2018/00625* (2013.01); *A61B 2018/142* (2013.01); *A61B 2018/1417* (2013.01)

(58) Field of Classification Search
CPC ........... A61B 2018/00601; A61B 2018/00625; A61B 2018/1417; A61B 2018/142
See application file for complete search history.

(56) References Cited

U.S. PATENT DOCUMENTS

| | | | | |
|---|---|---|---|---|
| 8,317,782 | B1* | 11/2012 | Ellman | .................. A61B 18/14 606/32 |
| 2003/0153906 | A1* | 8/2003 | Sharkey | ............... A61B 18/148 606/41 |
| 2009/0125021 | A1 | 5/2009 | Brommersma | |
| 2011/0066145 | A1 | 3/2011 | Epstein et al. | |
| 2012/0059219 | A1 | 3/2012 | St. George et al. | |
| 2014/0276757 | A1 | 9/2014 | Ellman | |
| 2014/0276801 | A1 | 9/2014 | Juergens et al. | |
| 2017/0100190 | A1* | 4/2017 | Gupta | .................. A61B 18/149 |

FOREIGN PATENT DOCUMENTS

| | | |
|---|---|---|
| WO | 95/10978 A1 | 4/1995 |
| WO | 02/11635 A1 | 2/2002 |
| WO | 2005/122938 A1 | 12/2005 |
| WO | 2013/070311 A1 | 5/2013 |

OTHER PUBLICATIONS

May 19, 2016 Office Action issued in German Patent Application No. 102015015314.5.

* cited by examiner

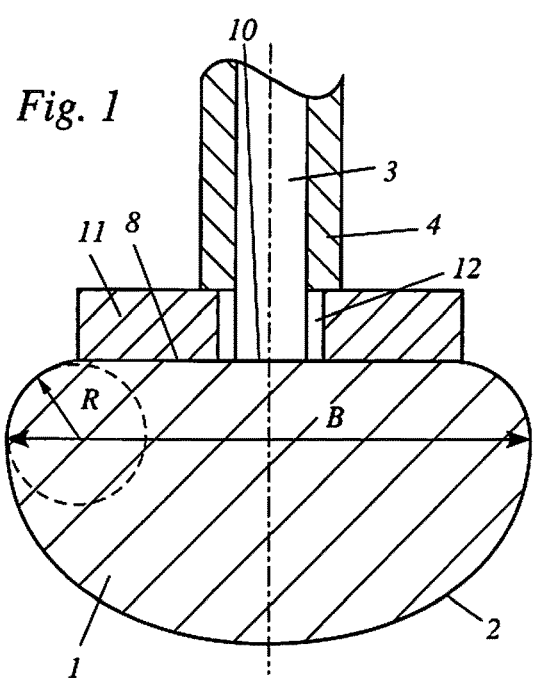
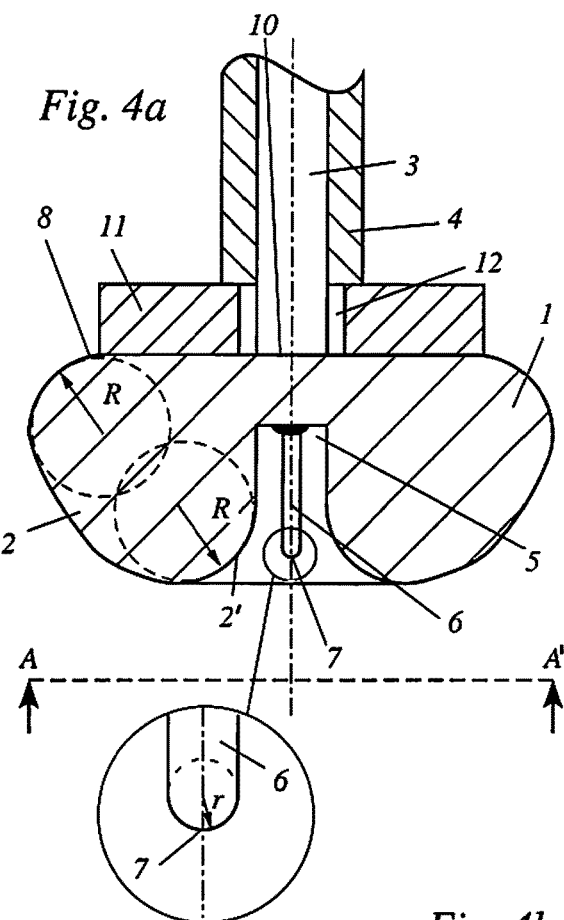
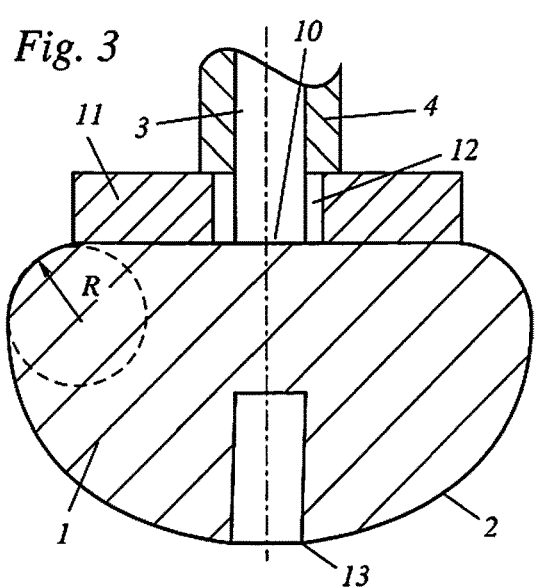
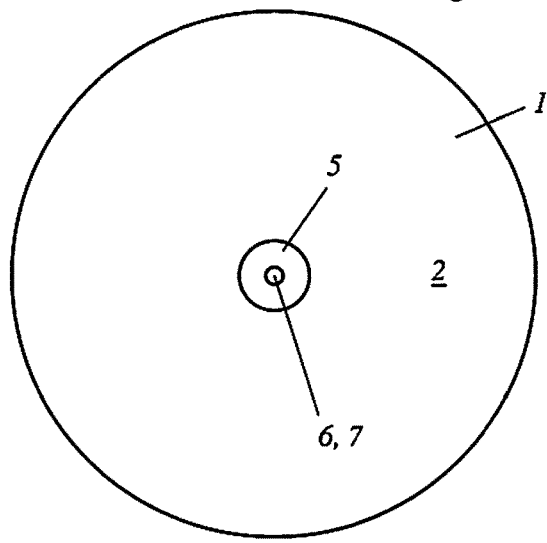
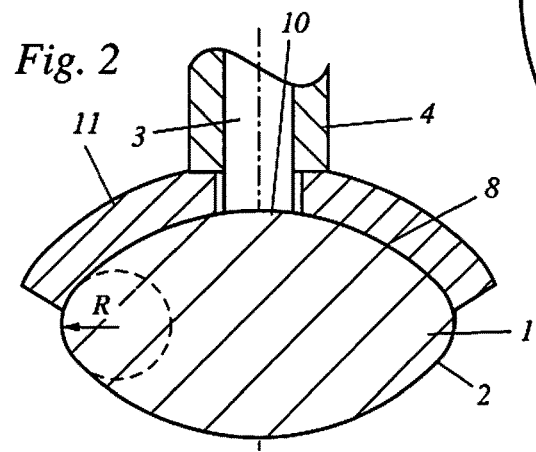

SURGICAL VAPORIZATION ELECTRODE

TECHNICAL FIELD

The invention relates to a surgical vaporization electrode.

STATE OF THE ART

From the state of the art, there are known electrical surgical resection tools, which are used for resection by passing a high-frequency (HF) alternating current through the part of the patient's body to be treated in order to locally and selectively excise the respective tissue. Such resection tools are used in particular to remove, for example, adenomatous tissue by vaporization. For this purpose, an HF voltage is generated by means of suitable HF generators and applied to the working part of the electrode by means of corresponding feeder lines, such electrodes being operated as bipolar electrodes or as monopolar electrodes, depending on their design.

The design most commonly used is the monopolar design, wherein one pole of the HF voltage source is connected to the patient over the largest possible area as a neutral electrode, and the surgical instrument (active electrode) forms the other pole. The current flows from the active electrode to the neutral electrode over the path of least resistance, so that the current density is highest in the immediate vicinity of the active electrode. Consequently, the thermal effect is strongest here, but adjacent tissue is also heated by the current flux.

In the bipolar technique, in contrast to the monopolar technique, the current flows through only a small portion of the body. The localized current density in the bipolar electrode causes rapid heating of the tissue surrounding the electrode tip, with subsequent vaporization of the tissue water or of the rinsing fluid (irrigation solution, saline) surrounding the tissue.

A thin layer of gas (steam cushion) forms around the electrode tip and can be ionized to form a constant plasma at a sufficiently high voltage (plasma ignition). The energy of the plasma is transferred to the cells of the tissue to be resected, resulting in locally limited vaporization of same. Tissue can be separated, i.e., removed more gently and more effectively by plasma vaporization than by traditional vaporization (e.g., by means of monopolar vaporization or by means of laser vaporization), because plasma vaporization requires contact between the electrode and the tissue only to the slightest extent and does not require high temperatures ("cold vaporization").

DE 102007054438 A1 describes a surgical vaporization electrode, preferably having a hemispherical electrode head, wherein the electrode head has a curved working surface (or working area) and at least one connection point, which is connected to a feeder wire enclosed in an insulating sheath. The surface region of the electrode head surrounding the connecting parts is provided with an insulating ceramic cover. The cover prevents plasma from being formed in other locations of the electrode head outside of the working area. Due to being embodied as a ceramic part, the cover is extremely stable both thermally and chemically.

WO 2013/070311 A1 describes a bipolar surgical resection tool, which is designed with either a hemispherical button electrode or an oval button electrode. The latter has an axial length in the working direction corresponding to the length of the hemispherical button electrode, while its (lateral) extent is much smaller, to thereby achieve an improved rate of tissue vaporization.

With the electrode heads known from the state of the art, the working surface of the electrode head is circumscribed by an edge. For example, with a hemispherical electrode head, this edge corresponds to the line of intersection between the spherical surface and the sectional surface of the hemisphere. A high current density prevails locally near this edge, so that vaporization begins there to an increased extent. Whereas tissue vaporization is desired primarily in the central portion of the working area or over a larger amount of surface of the working area, depending on the specific case, blistering and plasma activity occur to an increased extent in the edge region and thus at the boundary of the working area (working surface).

Depending on the size and shape of the surface of the vaporization electrode, the setting of the HF generator, the tissue impedance, the temperature of the rinsing fluid as well as the size of the tissue contact area, the ignition capacity of the plasma also increases. Because of the locally higher current density, a first plasma ignition is to be expected at the edge of the electrode, but this is often undesirable.

EXPLANATION OF THE INVENTION

In view of the aforementioned devices according to the prior art, the present invention is based on the object of providing a device, which does not have the aforementioned disadvantages or at least has them to a lesser extent. In particular a vaporization electrode, which does not facilitate vaporization and plasma ignition particularly in the boundary region of the working area, is to be created.

The invention relates to a surgical vaporization electrode having an electrical connecting line, which in turn has an electrically conductive electrode head that is electrically connected to the connecting line. The electrode head can be manufactured from the materials already known for manufacturing traditional button electrodes. The electrode head has a rear area (rear surface) facing the connecting line, a working area (working surface) that faces away from the connecting line and is planar or has a convex outward curvature and a curved boundary region, where the working area merges into the rear area without any actual edge. The respective local radius of curvature of the boundary region is nowhere smaller than one-thirtieth of the dimension of the electrode head in the direction of its maximum extent (i.e., for example, smaller than one-tenth of the radius of the sphere in the case of a hemispherical electrode head).

The fact that the rear area (rear surface) faces the connecting line means, in the given context, that the region of the connection between the connecting line and the electrode head is defined as the rear side of the electrode head. In contrast to the working surface, the rear surface is thus oriented essentially towards the direction of the electrode head, where the connecting line meets the electrode head.

The fact that the surgical vaporization electrode according to the invention has no edges or excessively narrow radii of curvature at the boundary of the electrode head results in blistering and plasma production being reduced in this region and activity of formation of gas and/or plasma being available primarily in the region of the working surface that is being used surgically.

The respective local radius of curvature of the boundary region is preferably not less than one-twentieth anywhere, in particular preferably not less than one-tenth of the dimension of the electrode head in the direction of its maximum extent.

The working surface, essentially corresponding, for example, to a section of a sphere or an ellipsoid, preferably has a convex curvature, but the working surface may also be designed to be flat. Due to the curvature, the angle between the electrode and/or the central axis of the electrode and the tissue may vary without having any mentionable negative effect on the resection effect. This in turn results in simpler handling.

According to a preferred embodiment, the connecting line serves as a holding arm for holding the electrode head and is designed to be stiff accordingly.

According to another preferred embodiment, the surgical vaporization electrode has an insulating cover, which partially or entirely covers the rear surface. Since plasma can form on any conducting surfaces of the vaporization electrode and not only on the working surface, the insulating cover advantageously prevents plasma from also forming on the rear surface close to the connecting line and its insulation sheathing, and thus prevents, on the one hand, the connecting line and/or the insulation material surrounding it from being damaged and, on the other hand, tissue vaporization from becoming less controllable. The insulating cover especially preferably comprises a ceramic material. The connecting line to the electrode head can be protected optimally from the influence of heat from the plasma by means of the heat resistance of the ceramic material.

According to an advantageous refinement of the invention, the surgical vaporization electrode has an electrode region, which is set back in comparison with the working surface (working area), such that the setback electrode region is bordered by a section of the working area on at least two sides, but preferably circumferentially. The setback electrode region may advantageously be designed as a recess in the working surface, in that the recess is, for example, drilled, sawed, milled, punched, etched or created as a gap between two or more electrode components arranged side by side. The setback electrode region may also be embodied as a curved pit (concave in particular) in the surface, which also forms the working area. For example, the setback electrode region may be created by a corresponding casting method, by means of a ram with a convex curvature or by ablation in the manufacture of the vaporization electrode.

According to a preferred embodiment of the advantageous refinement of the invention, at least one location in the transition between the working area and the setback electrode region has a local radius of curvature that is smaller than the minimum local radius of curvature of the boundary region. The transition between the working area and the setback electrode region especially preferably forms an actual edge. Because of increased local current densities, the plasma ignition predominantly takes place at the transition between the setback electrode region and the working area.

According to another preferred embodiment of the above advantageous refinement of the invention, an electrically conductive electrode element is provided in the setback electrode region; it is electrically connected to the connecting line and has a free end, wherein the electrically conductive electrode element has, at at least one location, preferably at its free end, a local radius of curvature that is smaller than the minimum local radius of curvature of the boundary region between the working area and the rear area. Because of the increased local current densities, the plasma ignition preferably takes place in the region of the electrically conductive electrode element. Accordingly, the free end of the electrode element preferably has a convex curvature or a conical shape. The free end of the electrically conductive electrode element preferably at least does not protrude beyond the bordering section of the working area and/or is set back with respect to the working area in order to be protected from mechanical stresses. In general, the electrically conductive electrode element and the working area (working surface) may be manufactured from one workpiece, or the electrically conductive electrode element is manufactured separately and inserted into the setback electrode region.

A vaporization electrode advantageously designed in such a manner, i.e., with an intentionally great local curvature in one location, permits instantaneous ignition of the plasma at the transition between the working surface and the setback electrode region and/or on the electrode element, which is in the shape of, for example, a mandrel, pin or stud in the setback region, because a higher electrical field intensity is generated on small surfaces and/or on surfaces with a small radius of curvature at the same voltage level (peak discharge effect). The higher current density thereby generated on the electrode element can create the gas pocket necessary for plasma ignition and can do so more rapidly, in a more stable manner and with a lower energy consumption around the vaporization electrode, even under less favorable conditions, for example, in activation in free rinsing fluid.

The invention is explained in greater detail below, by way of example referring to the accompanying schematic drawings. For illustrative purposes, the drawings are not drawn to scale, and in particular, the ratios of the individual dimensions to one another do not necessarily correspond to the ratios of the dimensions in actual technical implementations.

Several preferred exemplary embodiments are described, but the invention is not limited thereto. Generally, any embodiment of the invention, which is described and/or suggested within the present patent application may be particularly advantageous, depending on the economic, technical and medical specifics of the individual case. Unless otherwise explained to the contrary and/or inasmuch as it is fundamentally technically feasible, the individual features of the embodiments described herein are interchangeable or can be combined with one another and/or with features known per se from the prior art.

BRIEF DESCRIPTION OF THE FIGURES

FIG. 1 shows a cross sectional view of an exemplary embodiment of a surgical vaporization electrode according to the invention.

FIG. 2 shows another exemplary embodiment of a surgical vaporization electrode according to the invention in cross section.

FIG. 3 shows an exemplary embodiment of a surgical vaporization electrode according to the invention in a cross sectional view wherein a setback electrode region is embodied as a recess in the working area.

FIG. 4a shows an exemplary embodiment of a surgical vaporization electrode according to the invention in a cross sectional view wherein an electrically conductive electrode element is provided as an ignition aid in a setback electrode region. The region of the free end of the electrically conductive electrode element is also shown in an additional enlarged partial view.

FIG. 4b shows the vaporization electrode from FIG. 4a in a view from above, which is equivalent to projection of the working area and the conductive electrode element in the projection plane A-A' in FIG. 4a.

PREFERRED EMBODIMENT OF THE INVENTION

Corresponding elements are labeled with the same reference numerals in the various figures.

FIG. 1 shows the electrode head 1 of a surgical vaporization electrode, which may be designed in its other components like traditional vaporization electrodes known from the prior art, for example, DE 102007054438 A1.

The working area 2 (working surface) is made of a suitable high-temperature-resistant metal, as is also known for vaporization electrodes according to the prior art. In the exemplary embodiment, the working area 2 is designed to be essentially hemispherical but may also have any other shape, for example, an ovaloid or ellipsoid basic shape.

The electrode head 1 is supplied with voltage via an electrical connecting line 3, which is provided with an insulating sheathing 4 made of plastic. The connecting line 3 and the curved working area 2 are electrically connected to one another.

The electrical connecting line 3 is connected to a connecting site 10 on the electrode head 1 by welding or soldering, for example. The rear surface 8 of the electrode head 1 forming the spherical sectional surface is designed to be flat and is covered with a (generally optional) insulating cover 11 made of a ceramic material. The insulating cover 11 has a hole 12 through which the electrical connecting line 3 passes.

The transitional region from the working area 2 to the rear area 8 does not form an edge but instead is rounded with a minimum radius of curvature R which in the example shown here amounts to approximately one-seventh of the width B corresponding to the hemisphere parameter (=double hemisphere radius), which is the dimension of the electrode head 1 in the direction of its maximum extent. The relatively large radius of curvature R prevents the main activity of the electrode occurring at its margin due to excessively high local current densities.

The cover 11 may also be brought closer to the curved boundary region or may cover it entirely or partially.

The basic shape of the electrode head also need not necessarily be hemispherical. In the embodiment in FIG. 2, the electrode head 1 has a lenticular cross section in the cross-sectional plane shown here (=plane of the drawing). According to one variant, the electrode head 1 may be rotationally symmetrical so that the width perpendicular to the plane of the drawing is equal to the width in the plane of the drawing. According to an additional variant, the electrode head 1 in the plane may be perpendicular to the plane of the drawing but may also be elongated if it is desired for the working area 2 to be asymmetrical in the surgical application.

The electrode head 11 is embedded in the shell-shaped insulator cover 11.

In FIG. 2, the relatively large radius of curvature R at the transition between the working area 2 and the rear area 8 also prevents the formation of bubbles and plasma from occurring mainly at the margin of the electrode due to excessively high local current densities.

In the specific embodiments shown in FIGS. 3, 4a and 4b, an electrode region 5 formed by a recess that is setback with respect to the working area 2 is provided, bordered circumferentially by a section of the working area 2. The recess may be a simple borehole. Whereas in FIG. 3, the peripheral border of the setback electrode region 5 has an edge, in FIG. 4a the surface 2' forming the working area 2 bulges inward at the transition between the setback electrode region 5 and the working area 2. The radius of curvature need not necessarily correspond to the radius of curvature at the transition between the working area 2 and the rear area 8.

Apart from the setback electrode region 5, the specific embodiment shown in FIG. 3 largely corresponds to that in FIG. 1. The edge 13 at the transition between the setback electrode region 5 and the working area 2 permits instantaneous ignition of the plasma due to the so-called peak discharge effect. The higher current density locally can create more rapidly the gas pocket required for plasma ignition around the vaporization electrode and do so with a lower energy consumption, even under less favorable conditions, for example, in activation in a free rinsing fluid. Due to the lower required energy input, the temperature of the rinsing fluid is increased far less during ignition than is the case with a traditional button-shaped vaporization electrode.

In the specific embodiment in FIGS. 4a and 4b, a mandrel-shaped electrically conductive electrode element 6 having one free end 7 and the other end also electrically connected to the connecting line 6 is arranged in the setback electrode region 5. The free end 7 has a convex curvature and has a local radius of curvature r which is much smaller than the radius of curvature R at the transition between the working area 2 and the rear area 8.

The electrically conductive electrode element 6 has a surface area which is smaller than one-tenth of the surface area of the working surface 2—when considered in the projection plane A-A', in which the surface area of the working area 2 is at its maximum in comparison with other projection planes. The projection plane A-A' is any plane parallel to the sectional surface 8 of the sphere. The electrode element 6 is welded at the weld 9 in the setback electrode region 5 by means of laser welding but it may also be joined by means of other joining techniques, such as soldering, or it may be formed from the same material as the working area 2.

Due to the electrical field intensity, a gas pocket for generating a constant plasma is formed around the electrode element 6 in the setback electrode region 5 with little expenditure of energy. The electrode element 6 is of such dimensions that its free end 7 is set back with respect to the working area 2, i.e., it does not protrude beyond the bordering section of the working area 2. It is thus protected from mechanical damage.

The invention claimed is:
1. A surgical vaporization electrode, comprising:
an electrical connecting line;
an electrically conductive electrode head having:
  a rear area facing the electrical connecting line;
  a working surface electrically connected to the electrical connecting line and facing away from the electrical connecting line and being either planar or convexly outwardly curved;
  an electrode region, which is set back with respect to the working surface, such that the setback electrode region is bordered, on at least two sides thereof, by a section of the working surface; and
  a curved boundary region, where the working surface edgelessly merges into the rear area,
  wherein a minimum local radius of curvature of the boundary region is not smaller than one-thirtieth of a dimension of the electrode head in a direction of a maximum extent of the electrode head; and
an electrically conductive electrode element, which is arranged in the setback electrode region and is electrically connected to the electrical connecting line and which has a free end,
wherein the electrically conductive electrode element has, in at least one location thereof, a local radius of curvature that is smaller than the minimum local radius of curvature of the boundary region.

2. The surgical vaporization electrode according to claim 1,
wherein the minimum local radius of curvature of the boundary region is not smaller than one-twentieth of the dimension of the electrode head in the direction of a maximum extent of the electrode head.

3. The surgical vaporization electrode according to claim 2,
wherein the minimum local radius of curvature of the boundary region is not smaller than one-tenth of the dimension of the electrode head in the direction of a maximum extent of the electrode head.

4. The surgical vaporization electrode according to claim 1, wherein the electrical connecting line serves as a holding arm for holding the electrode head.

5. The surgical vaporization electrode according to claim 1, further comprising:
an insulating cover completely or partially covering the rear area.

6. The surgical vaporization electrode according to claim 1, wherein at least one location at a transition between the working surface and the setback electrode region has a local radius of curvature, which is smaller than the minimum local radius of curvature of the boundary region.

* * * * *